United States Patent
Mase et al.

[11] Patent Number: 6,130,232
[45] Date of Patent: Oct. 10, 2000

[54] SUBSTITUTED PIPERIDINE DERIVATIVES AS MUSCARINIC M₃ RECEPTOR ANTAGONISTS

[75] Inventors: Toshiaki Mase; Morihiro Mitsuya; Kensuke Kobayashi; Kazuhito Noguchi, all of Tsukuba, Japan

[73] Assignee: Banyu Pharmaceutical Coaltd, Tokyo, Japan

[21] Appl. No.: 09/051,287

[22] PCT Filed: Oct. 7, 1996

[86] PCT No.: PCT/JP96/02904

§ 371 Date: Apr. 9, 1998

§ 102(e) Date: Apr. 9, 1998

[87] PCT Pub. No.: WO97/13766

PCT Pub. Date: Apr. 17, 1997

[30] Foreign Application Priority Data

Oct. 13, 1995 [JP] Japan ................................. 7-291716
Dec. 26, 1995 [JP] Japan ................................. 7-351342

[51] Int. Cl.⁷ ..................... A61K 31/445; C07D 401/06
[52] U.S. Cl. .......................................... 514/318; 546/194
[58] Field of Search .................................. 514/256, 317, 514/318, 326; 546/194, 208, 209, 210, 213, 214, 222, 224

[56] References Cited

U.S. PATENT DOCUMENTS 5,750,540 5/1998 Tsuchiya ............................... 514/318
5,968,956 10/1999 Okada et al. .......................... 514/329

FOREIGN PATENT DOCUMENTS 0751127 1/1997 European Pat. Off. .
52-83763 7/1977 Japan .
56-79688 6/1981 Japan .
01131145 5/1989 Japan .
04500521 1/1992 Japan .
07216943 8/1995 Japan .
07258250 10/1995 Japan .

OTHER PUBLICATIONS

Chemical Abstracts, vol. 114, No. 91, Jan. 7, 1991, abstract No. 671, Tejani–But, Shanaz M. et al.

Scheithauer, S., Pharmazie, 43 (2), 86–90, 1988. "Synthesis of some metabolites of the bladder spasmolytic propiverine hydrochloride".

Japanese language publication "Seitai no Kagaku" (biochemistry), vol. 42(5), p. 380–385, 1991 and partial English translation.

Chem. Parm. Bull., vol. 32, No. 3, (1984), Sugia, Saburo et al, "Studies on Spasmolytics I. Synthesis and Spasmolytic . . . piperidines", p. 967–976.

Chem. Pharm. Bull., vol. 32, No. 3, (1984), Sugai, Saburo et al., "Studies on Spasmolytics. II. Synthesis . . . Compounds", p. 977–985.

Chem. Pharm. Bull., vol. 32, No. 3, (1984), Sugai, Saburo et al., "Studies on Spasmolytics. III. Synthesis . . . Salts", p. 1126–1134.

Chem. Pharm. Bull., vol. 33, No. 2, (1985), Yoshida, Seiichiro et al., "Structure–Activity Relationship . . . piperidine Derivatives", p. 818–822.

*Primary Examiner*—Ceila Chang

[57] ABSTRACT

This invention provides substituted heteroaromatic ring derivatives which are represented by a general formula [I] below:

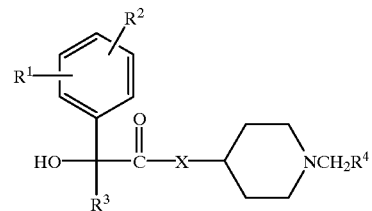

[in the formula, $R^1$ and $R^2$ may be same or different and each signifies hydrogen, halogen or lower alkyl; $R^3$ signifies $C_3$–$C_6$ cycloalkyl or cycloalkenyl; $R^4$ signifies a heteroaromatic ring group which may be condensed with a benzene ring and which has 1 or 2 hetero atoms selected from a group consisting of nitrogen, oxygen and sulfur atoms (said heteroaromatic ring group being optionally substituted with lower alkyl, halogen, lower alkoxy, amino or hydroxymethyl); and X stands for O or NH] or their pharmaceutically acceptable salts.

The substituted heteroaromatic ring derivatives of the present invention have selective $M_3$ muscarinic receptor antagonist activity, and hence they are useful as therapeutic or prophylactic agents which are safe and efficacious with little side effects, of respiratory diseases such as asthma, chronic airway obstruction and pulmonary fibrosis, etc.; urinary diseases which induce such urination disorders as pollakiurea, urgency and urinary incontinence, etc.; and gastrointestinal diseases such as irritable bowel syndrome, spasm of gastrointestinal tract and gastrointestinal hyperkinesis.

20 Claims, No Drawings

SUBSTITUTED PIPERIDINE DERIVATIVES AS MUSCARINIC $M_3$ RECEPTOR ANTAGONISTS

This application is the National Phase entry under 35 USC 371, of International PCT application PCT/JP96/02904, filed Oct. 7, 1996, and designating the United States.

TECHNICAL FIELD

This invention is useful in the field of drugs. More specifically, the novel substituted heteroaromatic ring derivatives of the invention are useful as therapeutic or prophylactic agents of various diseases of the respiratory, urinary and gastrointestinal systems. In particular, the compounds of the present invention do not affect other organs such as the brain and heart, although they exhibit potent bronchodilating and bladder contraction-suppressing actions. Hence they are useful as therapeutic or prophylactic agents of respiratory diseases such as asthma, chronic airway obstruction and pulmonary fibrosis, etc.; urinary diseases which induce such urination disorders as pollakiurea, urgency and urinary incontinence, etc.; and gastrointestinal diseases such as irritable bowel syndrome, spasm of gastrointestinal tract and gastrointestinal hyperkinesis.

BACKGROUND ART

Compounds having antagonism to muscarinic receptors are known to cause bronchodilation, gastrointestinal hypanakinesis, gastric hyposecretion, dry mouth, mydriasis, suppression of bladder contraction, hypohidrosis, tachycardia and the like [cf. *Seitai no Kagaku* (biochemistry), Vol. 42, p. 381 (1991)].

There are three subtypes of muscarinic receptors: $M_1$ receptors are present mainly in the brain, $M_2$ receptors, mainly in the heart, and $M_3$ receptors, on smooth muscles and glandular tissues. While a large number of compounds having antagonism to muscarinic receptors became known to date, those known compounds non-selectively antagonize the three subtypes of muscarinic receptors. Hence, attempts to use these compounds as therapeutic or prophylactic agents for diseases of the respiratory system have caused undesirable side effects such as tachycardia, dry mouth, nausea and mydriasis. In particular, side effects associated with the heart such as tachycardia induced by $M_2$ receptors pose problems, and their improvement has been in strong demand.

DISCLOSURE OF THE INVENTION

We have conducted concentrative research work on compounds which exhibit antagonism selective for $M_3$ muscarinic receptors, and have discovered that substituted heteroaromatic ring derivatives which are represented by formula [I] below:

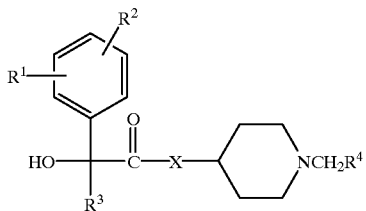

[I]

[in the formula, $R^1$ and $R^2$ may be same or different and each signifies hydrogen, halogen or lower alkyl; $R^3$ signifies $C_3$–$C_6$ cycloalkyl or cycloalkenyl; $R^4$ signifies a heteroaromatic ring group which may be condensed with benzene ring and which has 1 or 2 hetero atoms selected from a group consisting of nitrogen, oxygen and sulfur atoms (said heteroaromatic ring group being optionally substituted with lower alkyl, halogen, lower alkoxy, amino or hydroxymethyl); and X stands for O or NH]
are novel compounds never before described in literature and exhibit antagonism selective for $M_3$ muscarinic receptors; and that they are useful as safe and effective therapeutic or prophylactic agents exhibiting little side effects, of respiratory diseases such as asthma, chronic airway obstruction and pulmonary fibrosis, etc., urinary diseases which indue urination disorders such as pollakiurea, urgency and urinary incontinence, etc., and gastrointestinal diseases such as irritable bowel syndrome, spasm of gastrointestinal tract and gastrointestinal hyperkinesis. The present invention is thus completed.

Accordingly, therefore, the present invention relates to the substituted heteroaromatic ring derivatives which are represented by the general formula [I] and their pharmaceutically acceptable salts; their production processes and their use.

Definitions of terms used in this specification are explained hereinafter.

Halogen denotes fluorine, chlorine, bromine and iodine atoms.

Lower alkyl denotes $C_1$–$C_6$ linear or branched alkyl groups, eg., methyl, ethyl, propyl, isopropyl, butyl, sec-butyl, t-butyl, pentyl, isopentyl, hexyl and isohexyl.

Examples of $C_3$–$C_6$ cycloalkyl include cyclopropyl, cyclobutyl, cyclopentyl and cyclohexyl groups.

Examples of $C_3$–$C_6$ cycloalkenyl include cyclopropenyl, cyclobutenyl, cyclopentenyl and cyclohexenyl groups.

Lower alkoxy denotes $C_1$–$C_6$ linear or branched alkoxy groups, eg., methoxy, ethoxy, propoxy, isopropoxy, butoxy, sec-butoxy, t-butoxy, pentyloxy, isopentyloxy, hexyloxy and isohexyloxy groups, etc.

Lower alkoxycarbonyl denotes $C_2$–$C_7$ linear or branched alkoxycarbonyl groups, eg., methoxycarbonyl, ethoxycarbonyl, propoxycarbonyl, isopropoxycarbonyl, butoxycarbonyl, sec-butoxycarbonyl, t-butoxycarbonyl, pentyloxycarbonyl, isopentyloxycarbonyl, hexyloxy carbonyl and isohexyloxcarbonyl groups, etc.

Aralkyloxycarbonyl denotes $C_7$–$C_{10}$ aralkyloxycarbonyl groups, eg., benzyloxycarbonyl and phenetyloxycarbonyl groups, etc.

Protected hydroxyl and amino signify hydroxyl and amino groups which are protected with conventionally used protective groups such as acyl, etc.

Also deprotection signifies removal of protective groups by the means conventionally used in the field of organic chemistry, such as hydrolysis, hydrogenolysis and the like.

A heteroaromatic ring group which may be condensed with a benzene ring and which has 1 or 2 hetero atoms selected from a group consisting of nitrogen, oxygen and sulfur atoms (said heteroaromatic ring group being optionally substituted with lower alkyl, halogen, lower alkoxy, amino or hydroxymethyl) signifies, eg., 2-pyridyl, 3-pyridyl, 4-pyridyl, 2-thiazolyl, 2-thienyl, 3-thienyl, 1-imidazolyl, 2-imidazolyl, 3-imidazolyl, 4-imidazolyl, 3-pyrazolyl, 5-pyrazolyl, 2-furyl, 3-furyl, 2-pyrrolyl, 3-pyrrolyl, 2-pyrimidinyl, 4-pyrimidinyl, 5-pyrimidinyl, 2-pyrazinyl, 3-pyridazinyl, 4-pyridazinyl, 2-quinolinyl, 2-benzothienyl and 2-indolyl groups; which are optionally substituted with lower alkyl, lower alkoxy, amino or hydroxymethyl group.

For concretely explaining the present invention, furthermore, signification of each of the symbols used in the general formula [I] below:

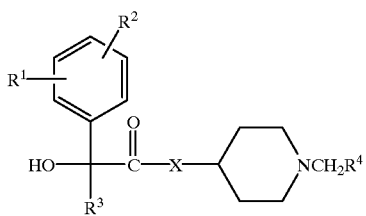

and their preferred examples are shown in the following.

$R^1$ and $R^2$ may be same or different and each signifies hydrogen, halogen or lower alkyl, where halogen signifies fluorine, chlorine, bromine or iodine atom; lower alkyl signifies $C_1-C_6$ linear or branched alkyl groups, for example, methyl, ethyl, propyl, isopropyl, butyl, sec-butyl, t-butyl, pentyl, isopentyl, hexyl and isohexyl groups, etc. Of those, hydrogen is preferred as $R^1$ and $R^2$.

$R^3$ signifies $C_3-C_6$ cycloalkyl or cycloalkenyl, wherein examples of $C_3-C_{16}$ cycloalkyl include, for example, cyclopropyl, cyclobutyl, cyclopentyl and cyclohexyl groups, and examples of $C_3-C_6$ cycloalkenyl include, for example, cyclopropenyl, cyclobutenyl, cyclopentenyl and cyclohexenyl. Of those, a cycloalkyl group is preferred as $R_3$, in particular, cyclopentyl is preferred.

$R^4$ signifies a heteroaromatic ring group which may be condensed with a benzene ring and which has 1 or 2 hetero atoms selected from a group consisting of nitrogen, oxygen and sulfur atoms (said heteroaromatic ring group being optionally substituted with lower alkyl, halogen, lower alkoxy, amino or hydroxymethyl), specific examples including 2-pyridyl, 3-pyridyl, 4-pyridyl, 2-thiazolyl, 2-thienyl, 3-thienyl, 1-imidazolyl, 2-imidazolyl, 3-imidazolyl, 4-imidazolyl, 3-pyrazolyl, 5-pyrazolyl, 2-furyl, 3-furyl, 2-pyrrolyl, 3-pyrrolyl, 2-pyrimidinyl, 4-pyrimidinyl, 5-pyrimidinyl, 2-pyrazinyl, 3-pyridazinyl, 4-pyridazinyl, 2-quinolinyl, 2-benzothienyl and 2-indolyl groups; which are optionally substituted with lower alkyl, halogen, lower alkoxy, amino or hydroxymethyl. Of those, 2-pyridyl group substituted with lower alkyl, halogen, amino or hydroxyl methyl, in particular, lower alkyl-substituted 2-pyridyl, inter alia 6-methyl-2-pyridyl group, is preferred.

X stands for O or NH, NH being the preferred.

The compounds of the present invention include optically active compounds, and their racemates.

Pharmaceutically acceptable salts of compounds of the general formula [I] signify those customary ones which are pharmaceutically acceptable. Examples of such acid addition salts include inorganic acid salts such as hydrochlorides, sulfates, nitrates, phosphates and perchlorates; organic acid salts such as maleates, fumarates, tartrates, citrates and ascorbates; sulfonic acid salts such as methanesulfonates, isethionates, benzenesulfonates and p-toluenesulfonates; and the like.

Next, production processes of the compounds of the present invention are explained.

Starting compounds to be used in the present invention are readily available or can be prepared by purchasing marketed products or by processing known starting materials following methods disclosed in literature [cf. Rzeszotarski, et al., *J. Med. Chem.*, Vol. 25, pp. 1103–1106 (1982), etc.]

Compounds of the general formula [I] can be prepared from starting compounds [III] following, for example, the reaction scheme illustrated below.

SCHEME 1

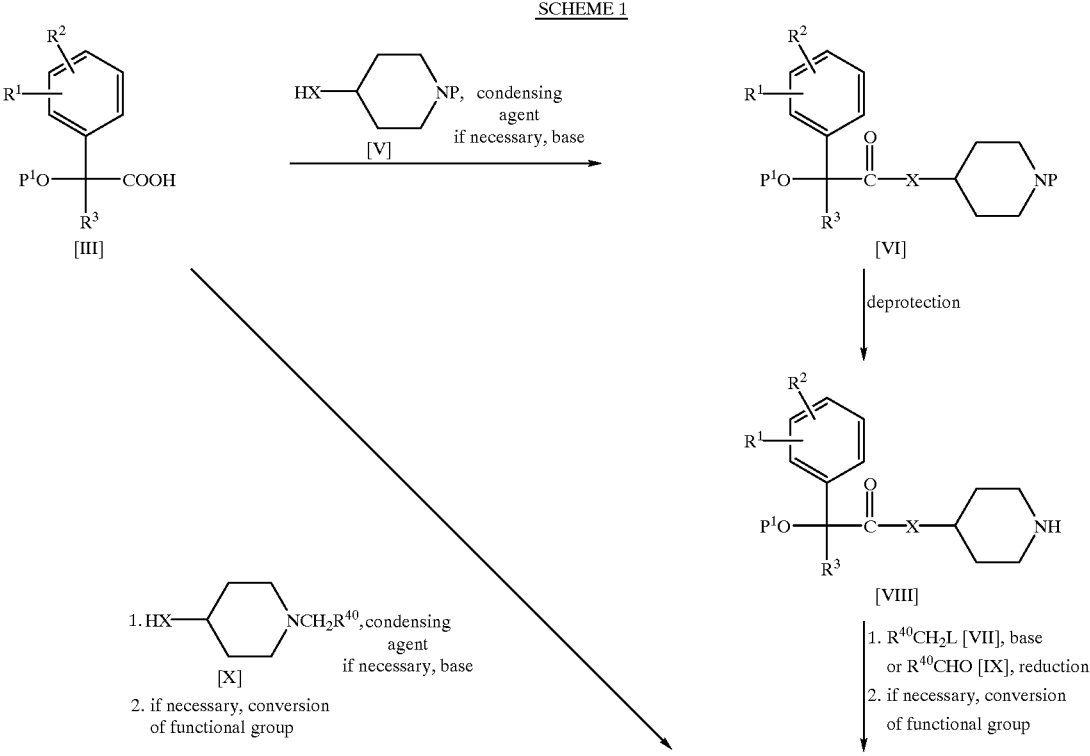

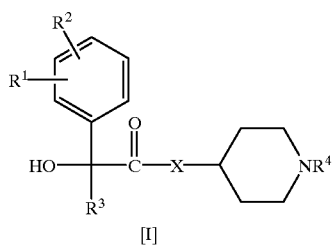

[I]

[in the formula, $R^1$, $R^2$, $R^3$ and $R^4$ have the previously given significations; $R^{40}$ signifies a heteroaromatic ring group which may be condensed with a benzene ring and which has 1 or 2 hetero atoms selected from a group consisting of nitrogen, oxygen and sulfur atoms (said heteroaromatic ring group being optionally substituted with lower alkyl, halogen, lower alkoxy, amino, protected amino, hydroxymethyl, protected hydroxymethyl, lower alkoxycarbonyl or aralkyloxycarbonyl); $P^1$ signifies a protective group of imino; P signifies hydrogen or a protective group of hydroxyl; L signifies a leaving group; and conversion of functional group signifies deprotection and/or reduction of lower alkoxycarbonyl or aralkyloxycarbonyl group to hydroxymethyl or conversion to amino].

The carboxylic acids represented by the general formula [III] can be readily prepared following, for example, S. B. Kadin, et al.'s method [J. Org. Chem., Vol. 27, pp. 240–245 (1962)].

The condensation reaction between a carboxylic acid of the general formula (III) with a protected piperidine derivative of the general formula [V] is conducted using generally approximately the equivalents of the reactants. If necessary, it is permissible to use either one of the reactants in excess. Again if necessary, the reaction can be conducted in the presence of a base. As condensing agents, those generally used in organic synthetic chemistry such as, for example, N,N'-dicyclohexylcarbodiimide, 1-ethyl-3-(3-dimethylaminopropyl)carbodiimide, diphenylphosphoryl azide, dipyridyldisulfide-triphenylphosphine, etc. are used. In particular, 1-ethyl-3-(3-dimethylaminopropyl) carbodiimide, etc. are preferred.

Said condensation reaction is preferably conducted using a solvent which is inert to the reaction. Examples of organic solvents useful for the occasion include diethyl ether, tetrahydrofuran, N,N-dimethylformamide, dioxane, benzene, toluene, chlorobenzene, methylene chloride, chloroform, carbon tetrachloride, dichloroethane, trichloroethylene and mixtures thereof. In particular, tetrahydrofuran, N,N-dimethylformamide and dioxane, etc. are preferred.

As bases used when the occasions demand, for example, aromatic amines such as pyridine, 4-dimethylaminopyridine, picoline, lutidine, quinoline, isoquinoline, etc. can be named. In particular, 4-dimethylaminopyridine is preferred.

The reaction temperature usually ranges from −70° C. to boiling point of the solvent used in the reaction, preferably between −20° C. and 100° C.

The reaction time usually ranges from 5 minutes to 7 days, preferably between 10 minutes and 24 hours.

The coupling reaction of a carboxylic acid of the general formula (III) with a protected piperidine derivative of the general formula [V] can be conducted also by first converting the carboxylic acid expressed by the general formula [III] to a reactive derivative and then reacting the same with a protected piperidine derivative of the general formula [V].

As such reactive derivatives, those generally used in organic synthetic chemistry such as mixed acid anhydrides, activated esters, eg., N-hydroxysuccinimide ester, etc. and activated amides eg., imidazolide, etc. may be named.

The reaction is generally conducted in an aprotonic solvent. Examples of useful solvent include halogenated hydrocarbons such as methylene chloride, chloroform, carbon tetrachloride, dichloroethane, trichloroethylene, etc.; ethers such as ethyl ether, tetrahydrofuran, dioxane, etc.; aromatic hydrocarbons such as benzene, toluene, chlorobenzene, xylene, etc.; aprotonic polar solvents such as dimethylformamide, acetonitrile, ethyl acetate, hexamethylphosphoric triamide, etc.; and their mixtures.

The reaction temperature usually ranges from −70° C. to boiling point of the solvent used in the reaction, preferably between −20° C. and 100° C.

The reaction time usually ranges from 5 minutes to 7 days, preferably between 10 minutes and 24 hours.

For smooth progress, the above reaction may be conducted in the presence of a base.

As the bases, for example, organic bases such as triethylamine, N-ethyldiisopropylamine, pyridine, 4-dimethylaminopyridine, N,N-dimethylaniline, 1,8-diazabicyclo[5.4.0]undec-7-ene (DBU) and 1,5-diazabicyclo-[4.3.0]non-5-ene (DBN), etc. may be named, in particular, 4-dimethylaminopyridine being preferred.

The amount of use of the base ranges from one mole to a molar excess, preferably 1 to 5 moles, per mole of a reactive derivatives of a carboxylic acid of the general formula [III].

Mixed acid anhydrides of compounds of the general formula [III] can be obtained, for example, by reacting the compounds with an alkyl chlorocarbonate, e.g., ethyl chlorocarbonate, an aliphatic carboxylic acid chloride, e.g., acetyl chloride, pivaloyl chloride or the like.

Activated esters of compounds of the general formula [III] can be obtained by reacting a carboxylic acid of formula [III] with an N-hydroxy compound, e.g., N-hydroxysuccinimide, N-hydroxyphthalimide or 1-hydroxybenzotriazole; or a phenol compound, e.g., 4-nitrophenol, 2,4-dinitrophenol, 2,4,5-trichlorophenol, pentachlorophenol or the like; in the presence of a condensing agent, e.g., N,N'-dicyclohexylcarbodiimide, 1-ethyl-3-(3-dimethylaminopropyl)carbodiimide, diphenylphosphoryl azide or dipyridyl disulfide-triphenylphosphine, according to conventional method.

Activated amides of compounds of the general formula [III] can be obtained by reacting a carboxylic acid of formula [III] with 1,1'-carbonyldiimidazole, 1,1'-carbonylbis(2-methylimidazole) or the like according to conventional method.

In particular, when X in the general formula [V] is 0, it is also possible to make a compound of the formula [VI] through an ordinary ester-exchange reaction between a lower alkyl ester of a carboxylic acid of the general formula [III] and an alcohol of the general formula [V].

A lower alkyl ester of a compound of the general formula [III] is obtainable by accepted methods, eg., by reacting a carboxylic acid of the general formula [III] with an excess of lower alcohol in the presence of an acid catalyst, or by using an esterification reagent such as diazomethane, trimethylsilyl-diazomethane or the like.

The ester-exchange reaction between a lower alkyl ester of a compound of the general formula [III] and a compound of the general formula [V] in which X is 0 is conducted following, eg., Rzeszotarski, et al's method [*Journal of Medicinal Chemistry*, Vol. 25, 1103–1106 (1982)] or the like.

Compounds represented by the general formula [VIII] can be derived by removal of imino-protective groups in compounds of the general formula [VI]. Useful imino-protective groups include aralkyl groups such as benzyl, p-methoxybenzyl, p-nitrobenzyl, benzhydryl and trityl; lower alkanoyl groups such as formyl, acetyl and propionyl; arylalkanoyl groups such as phenylacetyl and phenoxyacetyl; lower alkoxycarbonyl groups such as methoxycarbonyl, ethoxycarbonyl and t-butoxycarbonyl; alkenyloxycarbonyl groups such as 2-propenyloxycarbonyl; aralkyloxycarbonyl groups such as benzyloxycarbonyl and p-nitrobenzyloxycarbonyl; and lower alkylsilyl groups such as trimethylsilyl and t-butyldimethylsilyl, etc. In particular, t-butoxycarbonyl, benzyloxycarbonyl and the like are preferred.

Deprotection method of imino-protective groups differs depending on their kinds, and is conducted by the means following known method [cf. *Protective Groups in Organic Synthesis*, T. W. Greene, John Wiley & Sons Co. (1981)] or methods analogous thereto, for example, using acid or base, or by reducing means such as reduction using a metal hydride complex or catalytic hydrogenolysis.

Deprotection using an acid is generally conducted by treating the compound with an acid such as formic acid, trifluoroacetic acid, hydrochloric acid or sulfuric acid, in an inert solvent such as methylene chloride, anisole, tetrahydrofuran, dioxane, methanol or ethanol or a mixture of such a solvent with water, or in the absence of solvent, preferably at a temperature in the range from 0° to 100° C., for a period of time ranging from 10 minutes to 24 hours.

Deprotection using a base can generally be carried out by treating the compound with an alkali metal hydroxide, e.g., lithium hydroxide, sodium hydroxide or potassium hydroxide; an alkali metal carbonate, e.g., sodium carbonate or potassium carbonate, in an inert solvent which exerts no adverse effect on the reaction, e.g., methanol, ethanol, isopropanol, tetrahydrofuran or dioxane or a mixture of such a solvent with water, preferably at a temperature in the range of from −20 to 80° C., for a period of time ranging from 10 minutes to 24 hours.

Catalytic hydrogenolysis can generally be carried out in the presence of a catalyst such as palladium-on-carbon, palladium hydroxide, Raney nickel or platinum oxide, in an inert solvent, e.g., methanol, ethanol, water or acetic acid or a mixture of such solvents, preferably under a pressure of hydrogen of 1 to 20 kg/cm$^2$, preferably at a temperature in the range of from 0 to 40° C., for a period of time ranging from 10 minutes to 24 hours.

Alkylation of a deprotected compound of the general formula [VIII] with a compound of the general formula [VII] is conducted through a reaction at a temperature between 0° C. and boiling point of the employed solvent for 10 minutes to 48 hours, in the presence of 1–10 equivalents of an alkylation agent of the general formula [VII]; 1–10 equivalents, preferably 1–3 equivalents, of a base; and if necessary 0.1–10 equivalents, preferably 0.1–2 equivalents, of a reaction promotor; all the ratios being based on the deprotected body.

The reaction is usually conducted in an inert solvent. Examples of useful inert solvent include: ethers such as ethyl ether, tetrahydrofuran, dioxane and the like; aromatic hydrocarbons such as benzene, toluene, chlorobenzene, xylene and the like; aprotonic polar solvents such as dimethyl sulfoxide, N,N-dimethylformamide, acetonitrile, hexamethylphosphoric triamide and the like; and their mixtures.

As examples of leaving groups, halogen atoms, trifluoroacetoxy group, methanesulfonyloxy group, trifluoromethanesulfonyloxy group, p-toluenesulfonyloxy group, diphenoxyphosphoryloxy group and the like can be named. In particular, halogen atoms and methanesulfonyloxy group are preferred.

As the bases used for the reaction, for example, metal hydrides such as lithium hydride, sodium hydride, potassium hydride, etc.; metal hydroxides such as lithium hydroxide, sodium hydroxide, potassium hydroxide, etc.; alkali metal bicarbonates such as sodium hydrogencarbonate, potassium hydrogencarbonate, etc.; alkali metal carbonates such as sodium carbonate, potassium carbonate, etc.; tertiary aliphatic amines such as trimethylamine, triethylamine, N,N-diisopropylethylamine, N-methylmorpholine, N-methylpyrrolidine, N-methylpiperidine, N,N-dimethylaniline, 1,8-diazabicyclo-[5.4.0]undec-7-ene (DBU), 1,5-diazabicyclo [4.3.0]non-5-en (DBN), etc.; and aromatic amines such as pyridine, 4-dimethylaminopyridine, picoline, lutidine, quinoline, isoquinoline, etc. may be named. In particular, N,N-diisopropylethylamine and triethylamine are preferred.

As useful reaction promotors, alkali metal iodides such as lithium iodide, sodium iodide, potassium iodide, etc. can be named. In particular, potassium iodide is preferred.

Reductive alkylation of a deprotected compound of the general formula [VIII] with a compound of the general formula [IX] is generally conducted in an inert solvent which is not detrimental to the reaction. Examples of such inert solvent include alcohols such as methanol, ethanol, etc.; ethers such as ethyl ether, tetrahydrofuran, dioxane, etc.; aromatic hydrocarbons such as benzene, toluene, etc.; and mixed solvents thereof. For instance, methanol, ethanol, tetrahydrofuran and toluene are preferred.

The reaction temperature usually ranges from −30° C. to 200° C., preferably from 0° C. to 100° C.

The reaction time usually ranges from 10 minutes to 7 days, preferably from 10 minutes to 24 hours.

This reaction can be carried out under weakly acidic conditions which facilitate formation of Schiff bases. Acids which can be used for that purpose include, for example, p-toluenesulfonic acid, hydrochloric acid, acetic acid and trifluoroacetic acid.

The reducing reaction can be effected, for example, using a metal hydride complex such as sodium borohydride, sodium cyanoborohydride or lithium aluminum hydride, or by catalytic hydrogenation using a palladium-on-carbon catalyst, a Raney nickel catalyst or the like. Preferably, it is effected using a metal hydride complex such as sodium borohydride or sodium cyanoborohydride. Especially when the reducing reaction is carried out under weakly acidic conditions which facilitate formation of Schiff bases, it is preferable to use sodium cyanoborohydride or the like which are relatively stable under the acidic condition.

When a metal hydride complex is used as the reducing agent, the amount of reducing agent used may usually range from 1 mole to a molar excess, preferably from 1 to 10 moles, per mole of the compound of formula [IX].

The reaction of a compound of the general formula [III] or a reactive derivative thereof with a compound of the general formula [X] can be carried out in the manner similar to that between a compound of above general formula [III] or a reactive derivative thereof with a compound of the general formula [V].

Moreover, when a compound formed upon condensation of a compound of the general formula [III] or a reactive derivative thereof with a compound of the general formula [X], or a compound formed upon condensation of a compound of the general formula [VII] with a compound of the general formula [VII] or [IX] contains a protective group of functional group and/or lower alkoxycarbonyl or aralkyloxycarbonyl, a suitable functional group conversion needs to be conducted. Functional group conversion signifies removal of the protective group, reduction of the lower alkoxycarbonyl or aryloxycarbonyl group to hydroxymethyl or conversion to amino.

For the deprotection, above-described deprotection conditions can be suitably selected, depending on kind of the protective group. Reduction of a lower alkoxycarbonyl or aryloxycarbonyl group to hydroxymethyl can be effected through reduction using $LiAlH_4$ or the like, and the conversion to amino can be effected through a reaction which is generally referred to as Curtius reaction.

Isolation and purification of the general formula [I] compounds which are obtained through above-described processes can be effected by such usual separation methods as column chromatography, liquid chromatography or thin-layer chromatography, using silica gel, adsorbent resin or the like; solvent extraction or recrystallization and reprecipitation; performed either singly or in combination.

While the compounds of the present invention and their intermediates have optical isomers, this invention encompasses all of the optical isomers and their racemates.

When the compounds of the present invention and intermediates thereof are racemates, their optical resolution can be achieved by conventional means such as high-performance liquid chromatography using a chiral carrier, or fractional crystallization of diastereomeric salts thereof.

The compounds of formula [I] obtained in the above-described manner may be converted into pharmaceutically acceptable salts thereof according to accepted practice. Conversely, such salts may also be converted into the corresponding free amines according to accepted practice.

Hereinafter action of compounds of the present invention to inhibit binding to muscarinic receptors and their in vitro and in vivo antagonism to muscarinic receptors are described, to concretely indicate utility of the present invention. As the labelling ligand for $M_1$ muscarinic receptor, [$^3$H]-telenzepine was used and as that for $M_2$ and $M_3$ muscarinic receptors, [$^3$H]-N-methyl-scopolamine was used, and dissociation constants ($K_i$) were calculated from concentration of each of the tested compounds to inhibit binding of the labelling ligand by 50% ($IC_{50}$).

Test on Inhibition of Binding to Muscarinic Receptors

1) Making Membrane Preparations

Male SD strain rats weighing each 250 g–350 g [Japan Charles River K.K.] were sacrificed and their cerebral cortices, hearts and lacrimal glands were extirpated. The isolated organs were homogenized with Polytron (setting: 5) in an ice-cooled, 5-times diluted buffer solution (pH 7.4) containing 50 mM tris-hydrochloric acid, 5 mM magnesium chloride, 1 mM ethylenediamine-tetraacetic acid trisodium salt and 20% sucrose, followed by 15 minutes' centrifuge at 3,000×g and 4° C. After filtering the supernatant through gauze cloth, the filtrate was further subjected to an ultracentrifugation at 100,000×g at 4° C. for 45 minutes. The resultant precipitate was suspended in an ice-cooled buffer solution (pH 7.4, hereafter abbreviated as tris buffer) containing 50 mM tris-hydrochloric acid and 5 mM magnesium chloride. The suspension was subjected to an ultracentrifugation at 100,000×g at 4° C. for 45 minutes. The resultant precipitate was suspended in tris buffer at a concentration of 50 mg/ml and kept at −80° C. until the time of use. It was melted at the time of use in the binding inhibition tests.

2) Tests on Inhibition of $M_1$ Muscarinic Receptor Binding

These tests were performed according to a modification of the method of Hargreaves et al. (*Br. J. Pharmacol.* 107: pp. 494–501, 1992). Namely, a cerebral cortex membrane preparation, 1 nM [$^3$H]-telenzepine ([$^3$H]-Telenzepine, 85 Ci/mmol, New England Nuclear) and a test compound were incubated in 0.5 ml of tris buffer at room temperature (about 20–25° C.) for 120 minutes. Into the incubated system, 0.5 ml of ice-cooled tris buffer was added and suction-filtered with a glass filter (Packard Unifilter Plate GF/C). The filter was washed 4 times each with 1 ml of ice-cooled tris buffer. After drying the filter at 50° C. for an hour, a scintillator (Microscinti O: Packard Instrument Co., Inc.) was added and the radioactivity of the [$^3$H]-telenzepine which was adsorbed onto the filter was measured with a microplate scintillation counter (Top Count: Packard Instrument Co., Inc.). Non-specific binding of [$^3$H]-telenzepine to the receptors was determined under addition of 10 μM pirenzepine. Binding affinity of compounds of the present invention to $M_1$ muscarinic receptor was determined following the method of Cheng and Prussoff (*Biochem. Pharmacol.* 22: 3099–3108, 1973), ie., the dissociation constant ($K_i$) was calculated from the concentration ($IC_{50}$) of each test compound which achieved 50% inhibition of binding of [$^3$H]-telenzepine, the labelling ligand used.

3) Test on Inhibition of $M_2$ Muscarinic Receptor Binding

The test was conducted in the manner similar to above 2) $M_1$ muscarinic receptor binding inhibition test, except that the membrane preparations of the heart were used as the test specimens and 0.2 nM [$^3$H]-N-methylscopolamine ([$^3$H]-N-Methylscopolamine, 84 Ci/mmol, New England Nuclear) was used as the labelling ligand. Non-specific binding of [$^3$H]-N-methylscopolamine to the receptors was determined under addition of 1 μM N-methylscopolamine.

4) Test on Inhibition of $M_3$ Muscarinic Receptor Binding

The test was conducted in the manner similar to above 2) $M_1$ muscarinic receptor binding inhibition test, except that the membrane preparations of the lacrimal glands were used as the test specimens and 0.02 nM [$^3$H]-N-methylscopolamine was used as the labelling ligand. Non-specific binding of [$^3$H]-N-methylscopolamine to the receptor was determined under addition of 1 μM N-methylscopolamine.

TABLE 1

Inhibitory Effects on Binding to Muscarinic $M_1$, $M_2$ and $M_3$ Receptors

| | $K_i$ (nM) | | | | |
|---|---|---|---|---|---|
| | $M_1$ | $M_2$ | $M_3$ | $M_1$ / $M_3$ | $M_2$ / $M_3$ |
| Compound of Example 1 | 12 | 1100 | 2.9 | 4.3 | 380 |
| Compound of Example 9 | 29 | 1300 | 9.4 | 3.1 | 140 |
| Compound of | 16 | 1300 | 7.6 | 2.1 | 170 |

TABLE 1-continued

Inhibitory Effects on Binding to Muscarinic $M_1$, $M_2$ and $M_3$ Receptors

| | $K_i$ (nM) | | | | |
|---|---|---|---|---|---|
| | $M_1$ | $M_2$ | $M_3$ | $M_1/M_3$ | $M_2/M_3$ |
| Example 10 Compound of Example 11 | 11 | 730 | 8.8 | 1.3 | 83 |

As indicated in the above Table, the compounds of the present invention exhibited more potent antagonism to $M_3$ muscarinic receptor, than that to $M_1$ and $M_2$ muscarinic receptors.

Test-1 for Antagonism to Muscarinic Receptors (In Vitro)

1) Test for Antagonism to $M_1$ Receptor in an Isolated Rabbit Vas Deferens

This test was conducted following the method of Eltze, et al. [*European Journal of Pharmacology*, Vol. 151, pp. 205–221]. Male Japanese White rabbits (each weighing about 3 kg) were sacrificed by exsanguination from arteria femoralis under anesthetization with pentobarbital, and the vas deferens were isolated. As the vas deferens preparation, the part close to the prostate gland (1 cm in length) was used. The preparation was isometrically suspended in the direction of long axis in a Magnus tube filled with 20 ml of Krebs-Henseleit solution [gassed with 95% $O_2$-5% $CO_2$ and kept at 31° C., containing 1 μM yohimbine ($\alpha_2$ antagonist)] at an initial tension of 1.0 g and a resting tension of 0.75 g. The tension in each preparation was isometrically recorded. After 30 minutes' equilibration, contraction of the preparation under electric stimulation (0.5 ms, 30 V) using a bipolar electrode was caused at every 20 seconds. After the contraction caused by the electric stimulation became stable, contraction-inhibitory response caused by McN A-343 (2.5× $10^{-5}$M, an $M_1$-selective agonist) was observed three times (conditioning response). Washing the preparation with a fresh solution to recover it from the contraction, McN A-343 ($10^{-7}$-$10^{-5}$M) was cumulatively administered thereto from a low concentration to three-fold increased dose, until the maximum response was obtained, to obtain a control dose-response curve. The preparation was again washed with the fresh solution and recovered from the contraction, and thereafter treated with a test compound. Ten minutes after the treatment, again McN A-343 was cumulatively administered to the preparation. The response to McN A-343 was expressed based on the extent of contraction before the administration of McN A-343, which was set to be 100%. The antagonistic potency ($K_B$ value) of the test compound was determined from the degree of shift in the dose-response curve caused by the treatment with the test compound.

2) Test for Antagonis to $M_2$ Receptor in Isolated Rat Right Atrium

This test was conducted following the method of Wess, et al. [*British Journal of Pharmacology*, Vol. 102, pp. 246–250]. Male SD strain rats (weighing 200–300 g) were sacrificed by exsanguination and the right atrium was isolated. Each preparation was isometrically suspended in a Magnus tube filled with 20 ml of Krebs-Henseleit solution (gassed with 95% $O_2$-5% $CO_2$, at 32° C.) at an initial tension of 0.5 g. The heart rate was recorded with a heart rate counter. After the preparation was equilibrated for 30 minutes, carbachol ($10^{-9}$ to $10^{-6}$ M) was cumulatively administered from a low concentration to three-fold increased doses. Thus, a decrease in heart rate was measured to obtain a control dose-response curve. After the preparation was washed with fresh solution to recover the heart rate, a test compound was administered thereto. Ten minutes later, carbachol was cumulatively administered again. Carbachol-induced responses were expressed as percentages based on the heart rate before administration of carbachol as 100%. The antagonistic potency ($K_B$ value) of the test compound was determined from the degree of shift of the dose-response curve resulted from the treatment with individual test compound of the present invention.

3) Test for Antagonism to the Airway $M_3$ Receptor in an Isolated Rat Trachea

This test was conducted following the method of Berge, et al. [*European Journal of Pharmacology*, Vol. 233, pp. 279–284]. Male SD strain rats (200–300 g) were sacrificed by exsanguination and the trachea was isolated. Ring segments (2 mm wide) were cut out from the trachea and cut transversely at the anterior cartilage part to make open ring preparations. Each preparation was suspended in a Magnus tube filled with 5 ml of Krebs-Henseleit solution (gassed with 95% $O_2$-5% $CO_2$, at 37° C.) at an initial tension of 1.0 g and a resting tension of 0.6 g. The tension of the preparation was recorded isometrically. After being equilibrated for an hour, the preparation was made to contract twice by treatment with $10^{-4}$M carbachol, and the second contraction induced by carbachol was used as the reference contraction. After the preparation was washed with fresh solution to be recovered to the base line, a test compound was administered thereto (or no treatment was given). Ten minutes later, carbachol ($10^{-8}$ to $10^{-3}$ M) was cumulatively administered in three-fold increased doses to obtain a dose-response curve. The dose-response curve was plotted by expressing responses as percentages based on the reference contraction of the preparation as 100%. The antagonistic potency ($K_B$ value) of the test compound was determined from the degree of shift of the dose-response curve obtained by treatment with the test compound.

4) Test for Antagonism to the Intestinal Tract $M_3$ Receptor in Isolated Rat Ileum Male SD strain rats (200–300 g) were sacrificed by exsanguination, and the ileum was isolated and formed into 2 cm-long preparations. Each preparation was suspended in a Magnus tube filled with 20 ml of Krebs-Henseleit solution (gassed with 95% $O_2$-5% $CO_2$ at 30° C.) with a load of 0.5 g. Tension in the preparation was isotonically recorded. After an hour's equilibration, the preparation was contracted twice with $10^{-6}$M carbachol, the second contraction being recorded as the reference contraction. After the preparation was washed with fresh solution and recovered to the base line, a test compounds was administered thereto (or no treatment was given). Ten minutes later, carbachol ($10^{-8}$ to $10^{-3}$M) was cumulatively administered to the preparation from at a low concentration to three-fold increased dose to obtain a dose-response curve. The dose-response curve was plotted by expressing responses as percentages based on the reference contraction of the preparation which was set to be 100%. The antagonistic potency ($K_B$ value) of the test compound was determined from the degree of shift in the dose-response curve resulted from the treatment with the test compound.

5) Test for Antagonism to the Bladder $M_3$ Receptor in Isolated Rat Urinary Bladder This test was conducted following the method of Noronha-Blob, et al. [*Journal of Pharmacological Experimental Therapeutics*, Vol. 256, pp. 562–567]. Male SD strain rats (200–300 g) were sacrificed by exsanguination and the urinary bladder was isolated. The bladders were cut into four longitudinal unfold sections, to form about 10 mm-long preparations. Each preparation was suspended in a Magnus tube filled with 5 ml of Krebs-Henseleit solution (gassed with 95% $O_2$-5% $CO_2$ at 32° C.) at an initial tension of 0.5 g. The tension in the preparation was isometrically recorded. After an hour's equilibration, the preparation was contracted twice with $10^{-4}$M carbachol, the second contraction being recorded as the reference contraction. After the preparation was washed with fresh solution and recovered to the base line, a test compound was administered thereto (or no treatment was given). Ten minutes later, carbachol ($10^{-8}$ to $10^{-3}$M) was cumulatively administered to the preparation from at a low concentration to three-fold increased dose to obtain a dose-response curve. The dose-response curve was plotted by expressing responses as percentages based on the reference contraction of the preparation which was set to be 100%. The antagonistic potency ($K_B$ value) of the test compound was determined from the degree of shift in the dose-response curve resulted from the treatment with the test compound.

calculated, and the dose of the test compound which inhibited the airway resistance obtained before the drug administration by 50% was recorded as $ID_{50}$ value.

2) Test on Rat Bradycardia

Eight- to eleven-weeks-old Sprague-Dawley strain rats (300–400 g) were anesthetized by intraperitoneal injection of urethane (750 mg/kg) and α-chloralose (37.5 mg/kg), and their right carotid artery, left jugular vein and airway of the rat were cannulated. After the spontaneous respiration was completely suppressed with succinylcholine (5 mg/kg, s.c.), their heart rates were measured under artificial ventilation. After stable bradycardia induced by intravenous administration of acetylcholine (10 μg/kg) was observed, a test compound was intravenously administered. Five minutes later, bradycardia was induced once again with acetylcholine administration. The inhibition ratio to the bradyeardia obtained before the administration of the test compound was calculated, and the dose of the test compound which inhibited the bradycardia obtained before the drug administration by 50% was recorded as $ID_{50}$ value.

TABLE 2

| | Antagonism to Muscarinic Receptors (in vitro) | | | | | Selectivity | |
|---|---|---|---|---|---|---|---|
| | $K_B$ (nM) | | | | | (multiplication) | |
| | vas deferens $M_1$ | right atrium $M_2$ | airway $M_3$ | ileus $M_3$ | bladder $M_3$ | $M_1/M_3$ | $M_2/M_3$ |
| Compound of Example 1 | 63 | 1100 | 4.4 | 70 | 3.6 | 14*¹ 18*² | 250*¹ 310*² |

*¹vas deferens $M_1$ or right atrium $M_2$/airway $M_3$
*²vas deferens $M_1$ or right atrium $M_2$/bladder $M_3$ As indicated above, the compound of the present invention exhibited antagonism to muscarinic receptors of vas deferens $M_1$, atrium $M_2$, airway $M_3$, ileus $M_3$ and bladder $M_3$; in particular, exhibited potent antagonism to airway $M_3$ and bladder $M_3$ receptors. Moreover, the action was more selective for the airway and bladder $M_3$ receptors. That is, the compound of the present invention is a compound more selective for airway $M_3$ and bladder $M_3$ receptors.

Test 2 for Antagonism to Muscarinic Receptors (In Vivo)

1) Test for Airway Resistance Enhancement in Rats

Eight- to eleven-weeks-old Sprague-Dawley strain rats (300–400 g) were anesthetized with urethane (750 mg/kg, i.p.) and α-chloralose (37.5 mg/kg, i.p.). The bronchus of each rat was intubated, and the right jugular vein was cannulated for drug administration. After spontaneous respiration was completely suppressed with succinylcholine (5 mg/kg, s.c.), the airway resistance was measured under artificial ventilation by means of a Pulmonary Mechanics Model 6 (Buxco). After stable airway resistance increase induced by intravenous administration of acetylcholine (50 μg/kg) was observed, a test compound was administered intravenously. After 5 minutes, once again the airway resistance increase was induced with acetylcholine. The inhibition ratio of the tested compound on the airway resistance increase before administration of the test compound was

TABLE 3

| | Antagonism to Muscarinic Receptors (in vivo) | |
|---|---|---|
| | airway constriction $ID_{50}$ (mg/kg i.v.) | bradycardia $ID_{50}$ (mg/kg iv) |
| Compound of Example 1 | 0.037 | >3 |
| atropine | 0.0043 | 0.0037 |
| ipratropium | 0.0015 | 0.0018 |

As above-indicated, the compound of the present invention exhibited potent bronchodilation, and was selective over bradycardiac response in which $M_2$ muscarinic receptor participates and which is associated with such side-effects as tachycardia of conventional cholinolytic agents. Whereas, atropine and ipratropium, the control compounds, exhibited potent activities in both cases and their actions were non-selective.

Those compounds which are represented by the general formula [I] can be administered to patients orally or parenterally, and can be used as therapeutic or prophylactic agents of asthma, chronic airway obstruction and pulmonary fibrosis, etc.; urination disorders as pollakiurea, urgency and urinary incontinence, etc.; and gastrointestinal diseases such as irritable bowel syndrome, spasm of gastrointestinal tract and gastrointestinal hyperkinesis upon formulating them into preparation forms suitable for respective administration routes. In clinical use of compounds of the present invention, it is also permissible to incorporate pharmaceutically acceptable adjuvants and formulate the preparations into the forms suitable for intended administration. As the adjuvants to be used in such occasions, those commonly used in the filed of pharmaceutics can be used, examples of which include: gelatin, lactose, sucrose, titanium oxide, starch, crystalline cellulose, hydroxypropylmethylcellulose, carboxymethylcellulose, corn starch, microcrystalline wax, white petrolatum, magnesium aluminate metasilicate, anhydrous calcium phosphate, citric acid, trisodium citrate, hydroxypropyl cellulose, sorbitol, sorbitan fatty acid ester, polysorbate, sucrose fatty acid ester, polyoxyethylene, hardened castor oil, polyvinylpyrrolidone, magnesium stearate, light silicic anhydride, talc, vegetable oil, benzyl alcohol, gum arabic, propylene glycol, polyalkylene glycol, cyclodextrin and hydroxypropylcyclodextrin.

The dosage forms of pharmaceutical compositions prepared as mixtures with these adjuvants include solid preparations such as tablets, capsules, granules, powders and suppositories; liquid preparations such as syrups, elixirs and injections; and the like. These preparations may be formulated according to conventional techniques well-known in the field of pharmaceutics. Liquid preparations may be in a form which is dissolved or suspended in water or other suitable media immediately prior to use. In particular, injections may be in the form of a solution or suspension in physiological saline solution or a glucose solution. If desired, such injections may contain buffer agents and/or preservatives.

In these pharmaceutical compositions, a compound in accordance with the present invention may be present at a ratio of from 1.0 to 100% by weight, preferably 1.0 to 60% by weight, based on the total weight of the composition. These pharmaceutical compositions may additionally contain other therapeutically effective compounds.

When the compounds of the present invention are used as bronchodilators, their dosage level and dosage schedule may vary according to sex, age and body weight of individual patient, severity of symptoms, type and range of desired therapeutic activity, and the like. Generally for oral administration, they are preferably administered in a daily dose of 0.1 to 100 mg/kg for adults and this daily dose may be given at a time or in several divided doses. For parenteral administration, they are preferably administered in a daily dose of 0.001 to 10 mg/kg for adults and this daily dose may be given at a time or in several divided doses.

Hereinafter the present invention is more specifically explained with reference to working examples, it being understood that the examples are in no way limitative of the scope of the invention.

EXAMPLE 1

(2R)-N-[1-(6-methyl-2-pyridylmethyl)piperidin-4-yl]-2-cyclopentyl-2-hydroxy-2-phenylacetamide dihydrochloride Structural formula

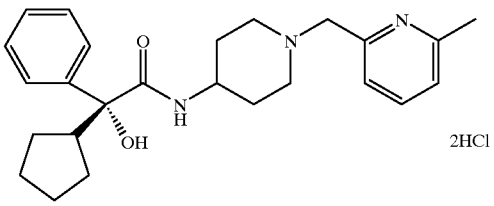

(1A) Synthesis of (2R)-2-cyclopentyl-2-hydroxy-2-phenylacetic acid by optical resolution Into a solution of 23.5 g of phenylglyoxylic acid ethyl ester in 200 ml of tetrahydrofuran, a diethyl ether solution of cyclopentyl magnesium chloride was added dropwise under ice cooling, followed by 30 minutes' stirring at the same temperature. Saturated aqueous ammonium chloride solution was added to the reaction mixture, and the reaction product was extracted with ethyl acetate, washed with saturated saline solution, and dried over anhydrous magnesium sulfate. Distilling the solvent off, the residue was purified by silica gel column chromatography (hexane/ethyl acetate=30/1 to 20/1). Thus 11 g of 2-cyclopentyl-2-hydroxy-2-phenylacetic acid ethyl ester was obtained, which was dissolved in 40 ml of methanol. To the solution 20 ml of 4N sodium hydroxide solution was added at room temperature, followed by 2 hours' stirring at the same temperature, and 1 hour's stirring at 50° C. Distilling the methanol off under reduced pressure, the aqueous layer was rendered weakly acidic with 4N hydrochloric acid and then extracted with ethyl acetate. The extract was washed with saturated saline solution, dried over anhydrous sodium sulfate and removed of the solvent by distillation. The resulting solid was washed with diethyl ether/hexane=1/1, and 8.7 g of 2-cyclopentyl-2-hydroxy-2-phenylacetic acid was obtained, which was dissolved, together with 11.6 g of cinchonidine, in 1.5 liters of toluene under heating, and the solution was cooled off to room temperature consuming about 4 hours. The white needles whereby precipitated were once again dissolved in 900 ml of toluene and cooled off to room temperature consuming about 4 hours. Recovering the precipitated white, acicular crystals by filtration, 8.0 g of (2R)-2-cyclopentyl-2-hydroxy-2-phenylacetic acid cinchonidine salt was obtained. The salt was dissolved in a mixture of diethyl ether and 1N hydrochloric acid, and the organic layer was washed with water and then with saturated saline solution, and dried over anhydrous magnesium sulfate. Distilling the solvent off under reduced pressure, 3.0 g of the title compound was obtained as a white solid (1B) Production of (2R)-2-cyclopentyl-2-hydroxy-2-phenylacetic acid by asymmetric synthesis To a solution of 293 mg of (2S,5S)-2-(t-butyl)-5-phenyl-1,3-dioxolan-4-one, which had been synthesized following the method of D. Seebach, et al. [*Tetrahedron*, Vol. 40, pp. 1313–1324 (1984)], in 10 ml of tetrahydrofuran, 1.0 ml of a hexane solution of 1.5 M lithium diisopropylamide was added dropwise at −78° C., followed by 30 minutes' stirring, addition of 0.15 ml of cyclopentanone, 1 hour's stirring at the same temperature and then addition of a solution of 510 mg of N-phenyltrifluoromethanesulfonimide in 5 ml of tetrahydrofuran. The reaction mixture was stirred overnight while being restored to room temperature. The resultant reaction mixture was poured into saturated aqueous ammonium chloride solution and extracted with ethyl acetate. The extract was washed with saturated saline solution, dried over anhydrous magnesium sulfate and removed of the solvent by reduced pressure distillation. The residue was purified by silica gel column chromatography (hexane/ethyl acetate=40/1), and 361 mg of an yellow oily substance was obtained, 113 mg of which was dissolved in 4 ml of methanol. To the solution 45 mg of sodium acetate and 15 mg of 10% palladium-on-carbon were added and stirred for 6 hours in a hydrogen atmosphere at normal pressure and room temperature. The reaction mixture was filtered through celite pad and removed of the solvent by reduced pressure distillation. To the residue ethyl acetate and saturated aqueous sodium hydrogencarbonate solution were added. The organic layer was separated, washed with saturated saline solution, dried over anhydrous magnesium sulfate and removed of the solvent by reduced pressure distillation. The residue was purified by preparative thin layer chromatography (Kieselgel™ 60F$_{254}$, Art 5744: Merck, hexane/ethyl acetate=19/1) to give 63 mg of a colorless oily substance. This product was dissolved in 1 ml of methanol, added with 1 ml of 1N sodium hydroxide solution and stirred for 3 hours at 60° C. Distilling the methanol off under reduced pressure, the remaining reaction mixture was washed with diethyl ether, made acidic with 1N hydrochloric acid and extracted with chloroform. The organic layer was washed with saturated saline solution, dried over anhydrous magnesium sulfate and removed of the solvent by reduced pressure distillation, to give 46 mg of the title compound as a white solid.

(2) Synthesis of 4-t-butoxycarbonylamino-1-(6-methyl-2-pyridylmethyl)piperidine

In 15 ml of dichloroethane, 315 mg of 4-t-butoxycarbonylaminopiperidine, 320 mg of 6-methyl-2-pyridinecarbaldehyde and 100 mg of acetic acid were dissolved. To the solution 575 mg of sodium triacetoxyborohydride was added at room temperature, followed by an hour's stirring at the same temperature. The reaction mixture was poured into saturated aqueous sodium hydrogencarbonate solution and extracted with chloroform. The extract was dried over anhydrous magnesium sulfate and removed of the solvent by reduced pressure distillation. The residue was purified by silica gel column chromatography (chloroform/methanol=100/1 to 50/1), to give 540 mg of the title compound as a white solid.

(3) Synthesis of 4-amino-1-(6-methyl-2-pyridylmethyl)-piperidine trihydrochloride In 20 ml of methanol, 540 mg of 4-t-butoxycarbonylamino-1-(6-methyl-2-pyridylmethyl)piperidine was dissolved, and to the solution 10 ml of 10% hydrogen chloride in methanol was added at room temperature, followed by 12 hours' stirring at the same temperature. Thereafter the solvent was distilled off under reduced pressure to give 530 mg of the title compound as a white solid.

(4) Synthesis of (2R)-N-[1-(6-methyl-2-pyridylmethyl)-piperidin-4-yl]-2-cyclopentyl-2-hydroxy-2-phenylacetamide To a solution of 110 mg of (2R)-2-cyclopentyl-2-hydroxy-2-phenylacetic acid, which had been obtained in Step (1A), in 8 ml of N,N-dimethylformamide, 95 mg of 1,1-carbonyldiimidazole was added at room temperature, and stirred for an hour at the same temperature. To the reaction mixture, further 180 mg of 4-amino-1-(6-methyl-2-pyridylmethyl)piperidine trihydrochloride as obtained in Step (3), 0.75 ml of triethylamine and 7.5 mg of 4-dimethylaminopyridine were added and stirred for 16 hours. The reaction mixture was poured into saturated aqueous solution of sodium hydrogencarbonate and extracted with diethyl ether. The extract was sequentially washed with water and saturated saline solution, dried over anhydrous magnesium sulfate and removed of the solvent by reduced pressure distillation. The residue was purified by silica gel column chromatography (chloroform/methanol= 50/1) to give 172 mg of the title compound as a white solid.

FAB-MS(m/e, (C$_{25}$H$_{33}$N$_3$O$_2$+H)$^+$): 408

$^1$H-NMR(CDCl$_3$) δ: 1.11–1.28 (1H, m), 1.36–1.90 (11H, m), 2.12–2.27 (2H, m), 2.53 (3H, s), 2.68–2.80 (2H, m), 2.95–3.09 (1H, m), 3.16 (1H, brs), 3.59 (2H, s), 3.65–3.80 (1H, m), 6.32 (1H, brd, J=8.1 Hz), 7.01 (1H, brd, J=7.3 Hz), 7.19 (1H, brd, J=7.6 Hz), 7.22–7.36 (3H, m), 7.48–7.63 (3H, m)

(5) Synthesis of (2R)-N-[1-(6-methyl-2-pyridylmethyl)-piperidin-4-yl]-2-cyclopentyl-2-hydroxy-2-phenylacetamide dihydrochloride 172 Milligrams of (2R)-N-[1-(6-methyl-2-pyridylmethyl) piperidin-4-yl]-2-cyclopentyl-2-hydroxy-2-phenylacetamide as obtained in Step (4) was dissolved in ethanol. To the solution 4N hydrogen chloride/ethyl acetate was added at room temperature and concentrated under reduced pressure. The residue was dissolved in a small amount of ethanol and solidified by addition of diethyl ether. The solid was recovered by filtration and dried under reduced pressure to give 145 mg of the title compound as a white solid.

$^1$H-NMR(CDCl$_3$) δ: 1.07–1.70 (8H, m), 1.81–2.08 (4H, m), 2.73 (3H, s), 3.01–3.34 (3H, m), 3.48–3.66 (2H, m), 3.84–3.98 (1H, m), 4.57 (2H, s), 7.18–7.34 (3H, m), 7.58–7.65 (2H, m), 7.68 (1H, brd, J=7.9 Hz), 7.72 (1H, brd, J=7.9 Hz), 8.16 (1H, t, J=7.9 Hz)

EXAMPLE 2

N-[1-(4-methyl-2-pyridylmethyl)piperidin-4-yl]-2-cyclopentyl-2-hydroxy-2-phenylacetamide (1) Synthesis of N-(1-t-butoxycarbonylpiperidin-4-yl)-2-cyclopentyl-2-hydroxy-2-phenylacetamide Structural formula

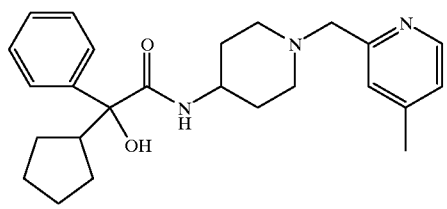

To a solution of 716 mg of 2-cyclopentyl-2-hydroxy-2-phenylacetic acid as obtained in Step (1A) of Example 1 in 5 ml of N,N-dimethylformamide, 540 mg of 1,1-carbonyldiimidazole was added at room temperature, and stirred for an hour at the same temperature. Further 846 mg of 4-amino-1-t-butoxycarbonylpiperidine hydrochloride and 1 ml of diisopropylethylamine were added, followed by 16 hours' stirring. The reaction mixture was poured into water and extracted with diethyl ether. The extract was sequentially washed with water and saturated saline solution, dried over anhydrous magnesium sulfate and removed of the solvent by reduced pressure distillation. The residue was purified by silica gel column chromatography (hexane/ethyl acetate=4/1 to 1/1) to give 752 mg of the title compound as a white solid.

(2) Synthesis of N-(piperidin-4-yl)- 2-cyclopentyl-2-hydroxy-2-phenylacetamide

752 Milligrams of N-(1-t-butoxycarbonylpiperidin-4-yl)-2-cyclopentyl-2-hydroxy-2-phenylacetamide was dissolved in 7 ml of 4N hydrogen chloride-dioxane solution, and stirred for 12 hours at room temperature. The reaction mixture was made weakly basic with 1N sodium hydroxide solution and extracted with diethyl ether. The extract was washed with saturated saline solution, dried over anhydrous magnesium sulfate and removed of the solvent by reduced pressure distillation to give 420 mg of the title compound as a white solid.

(3) Synthesis of N-[1-(4-methyl-2-pyridylmethyl) piperidin-4-yl]-2-cyclopentyl-2-hydroxy-2-phenylacetamide 75 Milligrams of 4-methyl-2-pyridinecarbaldehyde, 58.3 mg of N-(piperidin-4-yl)-2-cyclopentyl-2-hydroxy-2-phenylacetamide and 12 mg of acetic acid were dissolved in 10 ml of dichloroethane. To the solution 68 mg of sodium triacetoxyborohydride was added at room temperature, followed by an hour's stirring at the same temperature. The reaction mixture was poured into saturated aqueous sodium hydrogencarbonate solution, extracted with chloroform, dried over anhydrous magnesium sulfate and removed of the solvent by reduced pressure distillation. The residue was purified by preparative thin layer chromatography [Kieselgel™ 60F$_{254}$ Art 5744 (Merck), chloroform/methanol=9/1] to give 49.5 mg of the title compound as a white solid.

FAB-MS (m/e, $(C_{25}H_{33}N_3O_2+H)^+$): 408

$^1$H-NMR(CDCl$_3$) δ: 1.12–1.30 (1H, m), 1.37–1.74 (9H, m), 1.75–1.90 (2H, m), 2.12–2.26 (2H, m), 2.33 (3H. s), 2.69–2.80 (2H, m), 2.94–3.09 (1H, m), 3.15 (1H, s), 3.57 (2H, s), 3.65–3.80 (1H, m), 6.30 (1H, brd, J=8.4 Hz), 6.97 (1H, brd, J=5.3 Hz), 7.17 (1H, brs), 7.21–7.37 (3H, m), 7.58 (2H, brd, J=7.1 Hz), 8.39 (1H, d, J=5.3 Hz)

EXAMPLE 3

N-[1-(6-ethyl-2-pyridylmethyl)piperidin-4-yl]-2-cyclopentyl-2-hydroxy-2-phenylacetamide Structural formula

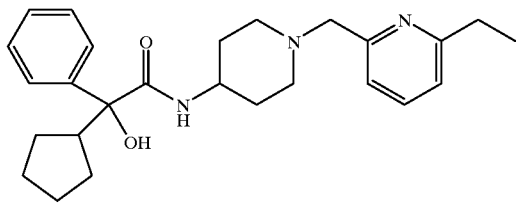

To a solution of 22 mg of 6-ethyl-2-pyridine-methanol in 3 ml of ethyl acetate, 0.1 ml of triethylamine and 50 μl of methanesulfonylchloride were added at room temperature, followed by 30 minutes' stirring at the same temperature. Saturated aqueous sodium hydrogencarbonate solution was added to the reaction mixture, followed by an hour's stirring. The organic layer was separated and the aqueous layer was extracted with ethyl acetate. The extract was combined with the organic layer, washed with saturated saline solution, dried over anhydrous magnesium sulfate and removed of the solvent by reduced pressure distillation. The residue was dissolved in 3 ml of N,N-dimethylformamide, and to the solution 32 mg of N-(piperidin-4-yl)-2-cyclopentyl-2-hydroxy-2-phenylacetamide as obtained in Step (2) of Example 2, 12 mg of sodium bromide and 85 mg of potassium carbonate were added, followed by 4 hours' stirring at room temperature. The reaction mixture was poured into water and extracted with diethyl ether. The extract was sequentially washed with water and saturated saline solution, dried over anhydrous magnesium sulfate and removed of the solvent by reduced pressure distillation. The residue was purified by preparative thin layer chromatography [Kieselgel™ 60F$_{254}$, Art 5744 (Merck), chloroform/methanol=12/1] to give 14.5 mg of the title compound as a white solid.

FAB-MS (m/e, $(C_{26}H_{35}N_3O_2+H)^+$) 422

$^1$H-NMR(CDCl$_3$) δ: 1.15–1.34 (1H, m), 1.29 (3H, t, J=7.5 Hz), 1.38–1.92 (11H, m), 2.17–2.30 (2H, m), 5 2.70–2.89 (2H, m), 2.81 (2H, q, J=7.5 Hz), 2.97–3.22 (2H, m) , 3.63 (2H, s), 3.67–3.81 (1H, m), 6.35 (1H, brd, J=7.7 Hz), 7.04 (1H, d, J=7.3 Hz), 7.21 (1H, d, J=7.9 Hz), 7.24–7.40 (3H, m), 7.53–7.65 (3H, m)

EXAMPLE 4

N-[1-(6-amino-2-pyridylmethyl)piperidin-4-yl]-2-cyclopentyl-2-hydroxy-2-phenylacetamide dihydrochloride Structural formula

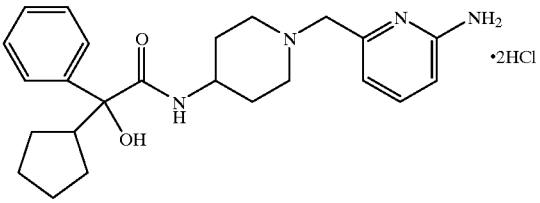

(1) Synthesis of N-[1-(6-ethoxycarbonyl-2-pyridylmethyl)piperidin-4-yl]-2-cyclopentyl-2-hydroxy-2-phenylacetamide Using 94 mg of 6-formyl-2-picolinic acid ethyl ester as the starting material by a method similar to Step (3) of Example 2, 191 mg of the title compound was obtained as a white solid.

(2) Synthesis of N-[1-(6-amino-2-pyridylmethyl) piperidin-4-yl]-2-cyclopentyl-2-hydroxy-2-phenylacetamide dihydrochloride To a solution of 40 mg of N-[1-(6-ethoxycarbonyl-2-pyridylmethyl)piperidin-4-yl]-2-cyclopentyl-2-hydroxy-2-phenylacetamide in 1 ml of methanol, 0.5 ml of 1N sodium hydroxide solution was added at room temperature, followed by 15 hours' stirring at the same temperature. The reaction mixture was made weakly acidic with 1N hydrochloric acid and concentrated under reduced pressure. The residue was dissolved in ethanol, and the insoluble matter was removed by filtration. The filtrate was concentrated under reduced pressure. The residue was purified by reverse phase ODS column chromatography (acetonitrile/water=2/1) to provide 27 mg of an oily substance. The product was dissolved in 1 ml of t-butanol. After addition of 20 mg of diphenylphosphoryl azide and 27 μl of triethylamine, the solution was refluxed for 18 hours. The solvent was distilled off, and the residue was purified by preparative thin layer chromatography [Kieselgel™ 60F$_{254}$, Art 5744 (Merck), chloroform/methanol=10/1] to give 14 mg of an oily substance. The product was dissolved in 0.5 ml of methanol, and to which 4N hydrogen chloride/dioxane was added at room temperature, followed by an overnight stirring. The reaction mixture was solidified by drying under reduced pressure to give 13 mg of the title compound as a white solid.

FAB-MS (m/e, ($C_{24}H_{22}N_4O_2$'+H): 409

$^1$H-NMR(CDCl$_3$) δ: 1.15–1.70 (19H, m), 1.79–1.90 (3H, m), 2.10–2.19 (2H, m), 2.68–2.78 (2H, m), 2.96–3.15 (2H, m), 3.47 (2H, s), 3.65–3.76 (1H, m), 6.33 (1H, d, J=8.2 Hz), 6.97 (1H, d, J=7.6 Hz), 7.23–7.36 (3H, m), 7.57–7.62 (3H, m), 7.78 (1H, d, J=8.3 Hz)

EXAMPLE 5

N-[1-(4-amino-2-pyridylmethyl)piperidin-4-yl]-2-cyclopentyl-2-hydroxy-2-phenylacetamide dihydrochloride Structural formula

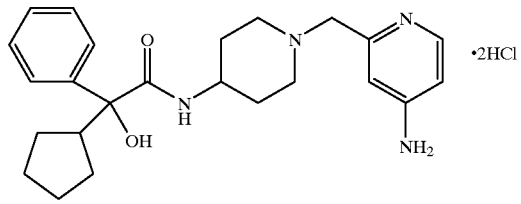

Using ethyl 2-formyl-4-picolinate as the starting material, a method similar to Example 4 was practiced to give 21 mg of the title compound as an yellow solid.

$^1$H-NMR(CDCl$_3$) δ: 1.20–1.75 (10H, m), 1.78–1.88 (1H, m), 2.10–2.25 (2H, m), 2.75–2.88 (2H, m), 3.01–3.13 (1H, m), 3.43 (2H, s), 3.54–3.67 (2H, m), 6.45 (1H, dd, J=2.3, 5.9 Hz), 6.65 (1H, d, J=2.3 Hz), 7.20 (1H, t, J=7.5 Hz), 7.29 (2H, t, J=7.5 Hz), 7.60 (2H, d, J=7.5 Hz), 7.88 (1H, d, J=5.9 Hz)

EXAMPLE 6

N-[1-(2-thienylmethyl)piperidin-4-yl]-2-cyclopentyl-2-hydroxy-2-phenylacetamide

Structural formula

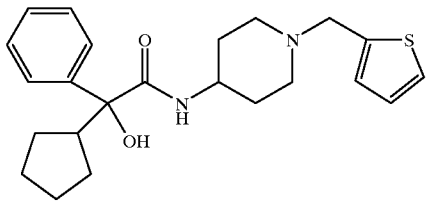

To a solution of 17 mg of 2-thiophenemethanol in 2 ml of chloroform, 4 drops of thionyl chloride were added, and stirred for 1 hour at room temperature. The solvent was distilled off and the residue was processed by a method similar to Example 3, to give 17 mg of the title compound as a colorless oily substance.

$^1$H-NMR(CDCl$_3$) δ: 1.13–1.74 (10H, m), 1.75–1.88 (2H, m), 2.05–2.18 (2H, m), 2.72–2.82 (2H, m), 2.94–3.07 (1H, m), 3.61–3.76 (1H, m),3.68 (2H, s), 6.29 (1H, brd, J=7.6 Hz), 6.87 (1H, d, J=4.2 Hz), 6.92 (1H, t, J=4.2 Hz), 7.21 (1H, d, J=4.2 Hz), 7.24–7.29 (1H, m), 7.34 (2H, t, J=7.1 Hz), 7.58 (2H, d, J=7.1 Hz)

EXAMPLE 7

N-[1-(4-hydroxymethyl-2-pyridylmethyl)piperidin-4-yl]-2-cyclopentyl-2-hydroxy-2-phenylacetamide Structural formula

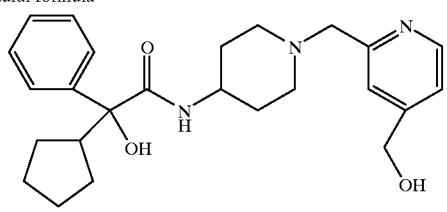

(1) Synthesis of N-[1-(4-ethoxycarbonyl-2-pyridylmethyl) piperidin-4-yl]-2-cyclopentyl-2-hydroxy-2-phenylacetamide Using 142 mg of 2-formyl-4-picolinic acid ethyl ester as the starting material and processing the same by a method similar to Step (3) of Example 2, 198 mg of the title compound was obtained as a colorless oily substance.

(2) Synthesis of N-[1-(4-hydroxymethyl-2-pyridylmethyl)piperidin-4-yl]-2-cyclopentyl-2-hydroxy-2-phenylacetamide To a solution of 92 mg of N-[1-(4-ethoxycarbonyl-2-pyridylmethyl)piperidin-4-yl]-2-cyclopentyl-2-hydroxy-2-phenylacetamide in 2 ml of tetrahydrofuran, 15 mg of aluminium lithium hydride was added at 0° C., followed by 2 hours' stirring at room temperature. To the reaction mixture 30 μl of 3N sodium hydroxide solution and anhydrous sodium sulfate were added, and the mixture was filtered with celite. Distilling the solvent off under reduced pressure, the residue was purified by preparative thin layer chromatography [Kieselgel™ 60F$_{254}$, Art 5744 (Merck), chloroform/methanol=10/1] to give 36 mg of the title compound as a colorless oily substance.

$^1$H-NMR(CDCl$_3$) δ: 1.10–2.28 (12H, m), 2.68–2.80 (2H, m), 2.95–3.08 (1H, m), 3.11–3.25 (1H, m), 3.60 (2H, s), 4.71 (2H, s), 6.38 (1H, d, J=8.2 Hz), 7.21–7.40 (4H, m), 7.59 (2H, d, J=8.4 Hz), 8.47 (1H, d, J=4.9 Hz)

EXAMPLE 8

N-[1-(6-methoxy-2-pyridylmethyl)piperidin-4-yl]-2-cyclopentyl-2-hydroxy-2-phenylacetamide Structural formula

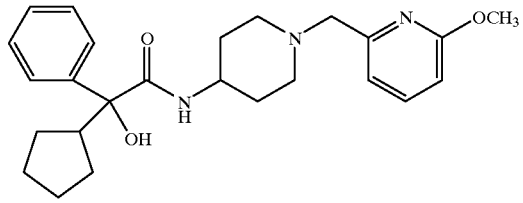

Using as the starting material 13 mg of 6-methoxy-2-pyridinecarbaldehyde which had been synthesized following the method of D. L. Comins, et al. [*J. Org. Chem.* Vol. 55, pp. 69–73 (1990)] in a method similar to Step (3) of Example 2, 37 mg of the title compound was obtained as a colorless oily substance.

FAB-MS (m/e, $(C_{25}H_{33}N_3O_3+H)^+$): 424

$^1$H-NMR(CDCl$_3$) δ: 1.10–1.75 (10H, m), 1.75–1.90 (2H, m), 2.15–2.30 (2H, m), 2.75–2.86 (2H, m), 2.95–3.08 (1H, m), 3.12 (1H, s), 3.55 (2H, s), 3.65–3.80 (1H, m), 3.90 (3H, s), 6.31 (1H, d, J=7.9 Hz), 6.59 (1H, d, J=8.2 Hz), 6.93 (1H, d, J=7.2 Hz), 7.22–7.38 (3H, m), 7.51 (1H, dd, J=7.2, 8.2 Hz), 7.56–7.62 (2H, m)

EXAMPLE 9

N-[1-(4-methoxy-2-pyridylmethyl)piperidin-4-yl]-2-cyclopentyl-2-hydroxy-2-phenylacetamide Structural formula

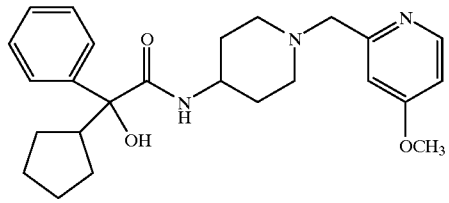

Using 21 mg of 4-methoxy-2-pyridinemethanol as a starting material in a method similar to Example 6, 13 mg of the title compound was obtained as a colorless oily substance.

FAB-MS (m/e, $(C_{25}H_{33}N_3O_3+H)^+$): 424

$^1$H-NMR(CDCl$_3$) δ: 1.10–1.75 (10H, m), 1.75–1.90 (2H, m), 2.12–2.28 (2H, m), 2.66–2.82 (2H, m), 2.93–3.09 (1H, m), 3.19 (1H, brs), 3.58 (2H, s), 3.65–3.80 (1H, m), 3.84 (3H, s), 6.34 (1H, d, J=7.9 Hz), 6.69 (1H, dd, J=2.5, 5.8 Hz), 6.93 (1H, d, J=2.5 Hz), 7.22–7.38 (3H, m), 7.56–7.62 (2H, m), 8.35 (1H, d, J=5.8 Hz)

EXAMPLE 10

N-[1-(6-chloro-2-pyridylmethyl)piperidin-4-yl]-2-cyclopentyl-2-hydroxy-2-phenylacetamide Structural formula

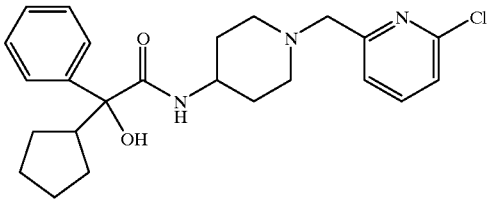

Using 19 mg of 6-chloro-2-pyridinemethanol as a starting material in a method similar to Example 6, 14 mg of the title compound was obtained as a white solid.

FAB-MS (m/e, $(C_{24}H_{30}ClN_3O_2+H)^+$): 428

$^1$H-NMR(CDCl$_3$) δ: 1.12–1.75 (10H, m), 1.75–1.91 (2H, m), 2.14–2.30 (2H, m), 2.67–2.80 (2H, m), 2.94–3.10 (1H, m), 3.09 (1H, s), 3.60 (2H, s), 3.84–3.80 (1H, m), 6.33 (1H, d, J=8.2 Hz), 7.19 (1H, d, J=7.8 Hz), 7.22–7.40 (4H, m), 7.56–7.64 (3H, m)

EXAMPLE 11

N-[1-(4-chloro-2-pyridylmethyl)piperidin-4-yl]-2-cylopentyl-2-hydroxy-2-phenylacetamide Structural formula

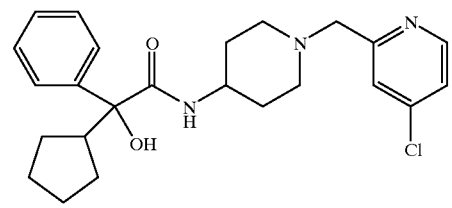

Using 20 mg of 4-chloro-2-pyridinecarbaldehyde as the starting material in a method similar to Step (3) of Example 2, 23 mg of the title compound was obtained as a white solid.

FAB-MS (m/e, $(C_{24}H_{30}ClN_3O_2+H)^+$): 428

$^1$H-NMR(CDCl$_3$) δ: 1.10–1.76 (10H, m), 1.76–1.91 (2H, m), 2.14–2.28 (2H, m), 2.65–2.82 (2H, m), 2.96–3.12 (2H, m), 3.60 (2H, s), 3.65–3.80 (1H, m), 6.33 (1H, d, J=8.5 Hz), 7.17 (1H, dd, J=2.1, 5.3 Hz), 7.22–7.38 (3H, m), 7.43 (1H, d, J=2.1 Hz), 7.56–7.64 (2H, m), 8.43 (1H, d, J=5.3 Hz)

EXAMPLE 12

N-[1-(2-quinolylmethyl)piperidin-4-yl]-2-cyclopentyl-2-hydroxy-2-phenylacetamide Structural formula

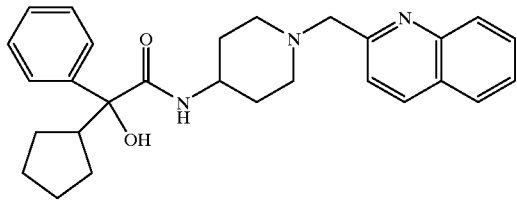

Using 19 mg of 2-quinolinecarbaldehyde as the starting material in a method similar to Step (3) of Example 2, 37 mg of the title compound was obtained as a white solid.

FAB-MS (m/e, $(C_{28}H_{33}N_3O_2+H)^+$): 444

$^1$H-NMR(CDCl$_3$) δ: 1.13–1.30 (1H, m), 1.48–1.75 (9H, m), 1.77–1.90 (2H, m), 2.20–2.32 (2H, m), 2.70–2.82 (2H, m), 2.95–3.09 (1H, m), 3.13 (1H, s), 3.66–3.82 (3H, m), 6.33 (1H, d, J=8.0 Hz), 7.22–7.38 (3H, m), 7.51 (1H, dd, J=1.1, 8.1 Hz), 7.56–7.62 (3H, m), 7.69 (1H, dd, J=1.1, 8.11 Hz), 7.79 (1H, d, J=8.1 Hz), 8.06 (1H, d, J=8.1 Hz), 8.1 (1H, d, J=8.1 Hz)

EXAMPLE 13

N-[1-(5-methyl-2-furylmethyl)piperidin-4-yl]-2-cyclopentyl-2-hydroxy-2-phenylacetamide Structural formula

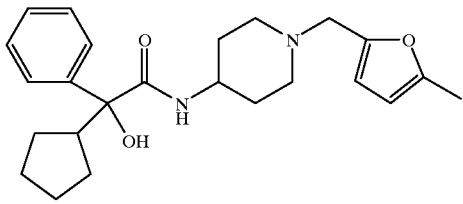

Using 11 mg of 5-methyl-2-furancarbaldehyde as the starting material in a method similar to Step (3) of Example 2, 18 mg of the title compound was obtained as a white solid.

FAB-MS (m/e, $(C_{24}H_{32}N_2O_3+H)^+$) 397

$^1$H-NMR(CDCl$_3$) δ: 1.12–1.75 (12H, m), 2.02–2.16 (2H, m), 2.26 (3H, s), 2.70–2.82 (2H, m), 2.94–3.08 (1H, m), 3.11 (1H, s), 3.43 (2H, s), 3.60–3.75 (1H, m), 5.85–5.90 (1H, m), 6.04 (1H, d, J=3.0 Hz), 6.28 (1H, d, J=8.3 Hz), 7.22–7.38 (3H, m), 7.55–7.62 (2H, 13m)

Industrial Applicability

The substituted heteroaromatic ring derivatives of the present invention exhibit selective M$_3$ muscarinic receptor antagonism. Hence, they are useful as therapeutic or prophylactic agents which are safe and efficacious with little side effects, for respiratory diseases such as asthma, chronic airway obstruction and pulmonary fibrosis, etc.; urinary diseases which induce such urination disorders as pollakiurea, urgency and urinary incontinence; and gastrointestinal diseases such as irritable bowel syndrome, spasm of gastrointestinal tract and gastrointestinal hyperkinesis.

What is claimed is:

1. A substituted heteroaromatic ring compound of formula (IA):

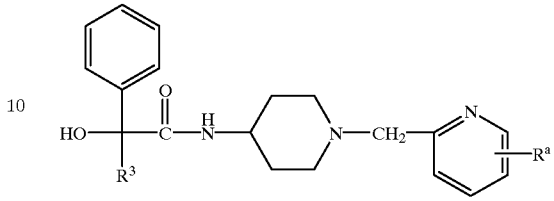

wherein

R$^3$ represents C$_3$ to C$_6$ cycloalkyl, and

R$^a$ represents lower alkyl, halogen, lower alkoxy or amino, or a pharmaceutically acceptable salt thereof.

2. A substituted heteroaromatic ring compound of formula (IB):

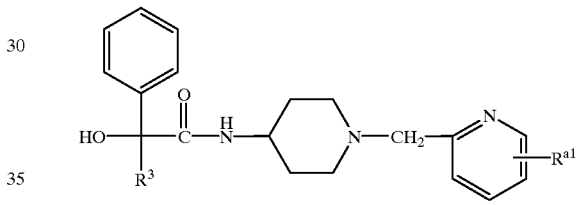

wherein

R$^3$ represents C$_3$ to C$_6$ cycloalkyl, and

R$^{a1}$ represents lower alkyl or amino, or a pharmaceutically acceptable salt thereof.

3. A substituted heteroaromatic ring compound of formula (IC):

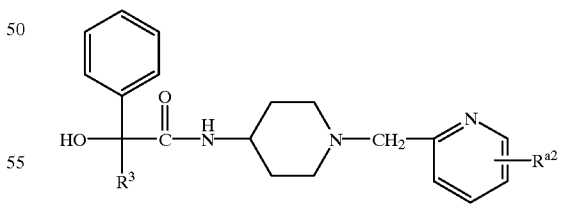

wherein

R$^3$ represents C$_3$ to C$_6$ cycloalkyl, and

R$^{a2}$ represents lower alkyl, or a pharmaceutically acceptable salt thereof.

4. A substituted heteroaromatic ring compound of formula (ID):

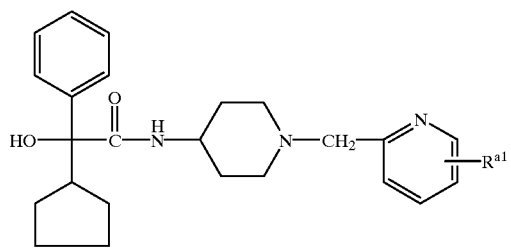

wherein $R^a$ represents lower alkyl, halogen, lower alkoxy or amino, or a pharmaceutically acceptable salt thereof.

5. A pharmaceutical composition exhibiting antagonism selective for $M_3$ muscarinic receptors, comprising a compound of formula (IA) as set forth in claim 1, or a pharmaceutically acceptable salt thereof, and at least one pharmaceutically acceptable adjuvant.

6. A pharmaceutical composition exhibiting antagonism selective for $M_3$ muscarinic receptors, comprising a compound of formula (IB) as set forth in claim 2, or a pharmaceutically acceptable salt thereof, and at least one pharmaceutically acceptable adjuvant.

7. A pharmaceutical composition exhibiting antagonism selective for $M_3$ muscarinic receptors, comprising a compound of formula (IC) as set forth in claim 3, or a pharmaceutically acceptable salt thereof, and at least one pharmaceutically acceptable adjuvant.

8. A pharmaceutical composition exhibiting antagonism selective for $M_3$ muscarinic receptors, comprising a compound of formula (ID) as set forth in claim 4, or a pharmaceutically acceptable salt thereof, and at least one pharmaceutically acceptable adjuvant.

9. The composition of claim 5 wherein the amount of the compound of formula (IA) is from 1.0 to 60 percent by weight of the composition.

10. The composition of claim 6 wherein the amount of the compound of formula (IB) is from 1.0 to 60 percent by weight of the composition.

11. The composition of claim 7 wherein the amount of the compound of formula (IC) is from 1.0 to 60 percent by weight of the composition.

12. The composition of claim 8 wherein the amount of the compound of formula (ID) is from 1.0 to 60 percent by weight of the composition.

13. A method for treatment or prophylaxis of respiratory diseases, urinary disorders, or gastrointestinal system diseases, wherein the disease or disorder is associated with muscarinic $M_3$ receptors, comprising administering to a patient in need thereof, an antagonistic effective amount, selective for muscarinic M3 receptor, of a compound of formula (IA) as set forth in claim 1 or a pharmaceutically acceptable salt thereof.

14. A method for treatment or prophylaxis of respiratory diseases, urinary disorders, or gastrointestinal system diseases, wherein the disease or disorder is associated with muscarinic $M_3$ receptors, comprising administering to a patient in need thereof, an antagonistic effective amount, selective for muscarinic M3 receptor, of a compound of formula (IB) as set forth in claim 2 or a pharmaceutically acceptable salt thereof.

15. A method for treatment or prophylaxis of respiratory diseases, urinary disorders, or gastrointestinal system diseases, wherein the disease or disorder is associated with muscarinic $M_3$ receptors, comprising administering to a patient in need thereof, an antagonistic effective amount, selective for muscarinic M3 receptor, of a compound of formula (IC) as set forth in claim 3 or a pharmaceutically acceptable salt thereof.

16. A method for treatment or prophylaxis of respiratory diseases, urinary disorders, or gastrointestinal system diseases, wherein the disease or disorder is associated with muscarinic $M_3$ receptors, comprising administering to a patient in need thereof, an antagonistic effective amount, selective for muscarinic M3 receptor, of a compound of formula (ID) as set forth in claim 4 or a pharmaceutically acceptable salt thereof.

17. The method according to claim 13 wherein the disease or disorder is asthma, chronic airway obstruction, pulmonary fibrosis, urination disorder, irritable bowel syndrome, spasm of gastrointestinal tract or gastrointestinal hyperkinesis.

18. The method according to claim 14 wherein the disease or disorder is asthma, chronic airway obstruction, pulmonary fibrosis, urination disorder, irritable bowel syndrome, spasm of gastrointestinal tract or gastrointestinal hyperkinesis.

19. The method according to claim 15 wherein the disease or disorder is asthma, chronic airway obstruction, pulmonary fibrosis, urination disorder, irritable bowel syndrome, spasm of gastrointestinal tract or gastrointestinal hyperkinesis.

20. The method according to claim 16 wherein the disease or disorder is asthma, chronic airway obstruction, pulmonary fibrosis, urination disorder, irritable bowel syndrome, spasm of gastrointestinal tract or gastrointestinal hyperkinesis.

* * * * *